(12) United States Patent
Furlano et al.

(10) Patent No.: US 9,090,647 B2
(45) Date of Patent: Jul. 28, 2015

(54) CRYSTALLINE FORMS OF REBAUDIOSIDE B

(75) Inventors: Bruce Michael Furlano, Vernon Hills, MN (US); Allan S. Myerson, Chicago, IL (US); Andrew Keith Ohmes, Jordan, MN (US); Troy Allen Rhonemus, Plymouth, MN (US); Christopher Austin Tyler, Minnetonka, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 13/993,378

(22) PCT Filed: Dec. 7, 2011

(86) PCT No.: PCT/US2011/063751
§ 371 (c)(1),
(2), (4) Date: Jun. 12, 2013

(87) PCT Pub. No.: WO2012/082493
PCT Pub. Date: Jun. 21, 2012

(65) Prior Publication Data
US 2013/0267693 A1    Oct. 10, 2013

Related U.S. Application Data

(60) Provisional application No. 61/422,370, filed on Dec. 13, 2010.

(51) Int. Cl.
*C07H 15/24*    (2006.01)

(52) U.S. Cl.
CPC ....................................... *C07H 15/24* (2013.01)

(58) Field of Classification Search
CPC ....................................................... C07H 15/24
See application file for complete search history.

(56) References Cited

U.S. PATENT DOCUMENTS 7,838,044 B2    11/2010  Abelyan et al.
2007/0292582 A1*  12/2007  Prakash et al. ................ 426/548
2010/0099857 A1    4/2010  Evans et al.
2010/0137569 A1    6/2010  Prakash et al.

FOREIGN PATENT DOCUMENTS

WO    2009137838 A1    11/2009
WO    2009140394 A1    11/2009

* cited by examiner

*Primary Examiner* — Elli Peselev

(57) ABSTRACT

A process for production of crystalline rebaudioside B from rebaudioside A is described. Additionally, four distinct crystal polymorphic forms of rebaudioside B are described, as well as methods for converting from one crystal polymorphic form of rebaudioside B to another crystal polymorphic form of rebaudioside B.

7 Claims, 17 Drawing Sheets

FIG. 3

| 2θ (°) | Intensity (%) | 2θ (°) | Intensity (%) |
|---|---|---|---|
| 8.5 | 29 | 24.8 | 34 |
| 11.3 | 20 | 25.5 | 16 |
| 12.6 | 18 | 27.6 | 13 |
| 13.5 | 26 | 28.1 | 16 |
| 14.3 | 40 | 29.1 | 20 |
| 15.5 | 51 | 29.3 | 23 |
| 15.8 | 39 | 29.5 | 24 |
| 16.7 | 35 | 30.5 | 17 |
| 17.7 | 100 | 31.0 | 20 |
| 18.5 | 20 | 31.7 | 18 |
| 19.2 | 30 | 32.0 | 18 |
| 19.9 | 75 | 33.6 | 16 |
| 21.1 | 17 | 34.8 | 13 |
| 21.8 | 21 | 35.7 | 18 |
| 22.5 | 82 | 37.2 | 14 |
| 23.7 | 19 | 37.7 | 14 |
| 24.0 | 15 | 39.2 | 33 |

FIG. 7

| 2θ (°) | Intensity (%) | 2θ (°) | Intensity (%) |
|---|---|---|---|
| 5.1 | 100% | 19.5 | 66 |
| 6.7 | 41 | 21.7 | 79 |
| 9.2 | 31 | 22.2 | 74 |
| 10.3 | 16 | 22.7 | 86 |
| 11.4 | 76 | 23.6 | 57 |
| 12.1 | 60 | 23.9 | 36 |
| 12.7 | 51 | 24.4 | 36 |
| 13.1 | 31 | 25.3 | 31 |
| 14.5 | 89 | 26.3 | 34 |
| 15.5 | 85 | 27.0 | 30 |
| 16.2 | 63 | 27.7 | 31 |
| 16.9 | 52 | 28.3 | 26 |
| 17.5 | 88 | 30.5 | 41 |
| 17.8 | 42 | 31.1 | 29 |
| 18.2 | 50 | 33.1 | 29 |
| 19.0 | 57 | 34.7 | 32 |

FIG. 11

| 2θ (°) | Intensity (%) | 2θ (°) | Intensity (%) |
|---|---|---|---|
| 4.8 | 100 | 21.9 | 7 |
| 6.4 | 31 | 22.5 | 5 |
| 8.9 | 9 | 23.3 | 8 |
| 10.0 | 5 | 24.1 | 8 |
| 11.1 | 8 | 24.9 | 4 |
| 11.8 | 6 | 26.0 | 4 |
| 12.4 | 6 | 26.5 | 5 |
| 12.8 | 8 | 27.5 | 5 |
| 14.2 | 13 | 28.1 | 5 |
| 14.3 | 10 | 30.3 | 6 |
| 15.3 | 12 | 30.8 | 4 |
| 15.9 | 7 | 32.7 | 5 |
| 16.6 | 8 | 33.0 | 4 |
| 17.3 | 28 | 34.0 | 6 |
| 17.9 | 18 | 35.3 | 3 |
| 18.6 | 8 | 34.3 | 4 |
| 19.3 | 27 | | |

FIG. 15

| 2θ (°) | Intensity (%) |
|---|---|
| 3.6 | 100% |
| 7.5 | 7% |
| 15.1 | 28% |
| 18.9 | 32% |
| 13.9 | 1% |
| 17.4 | 1% |
| 16.4 | 1% |
| 20.8 | 1% |
| 22.7 | 2% |
| 24.5 | 2% |
| 26.5 | 2% |
| 30.9 | 1% |
| 38.6 | 2% |

CRYSTALLINE FORMS OF REBAUDIOSIDE B

CROSS REFERENCE TO RELATED APPLICATIONS

"This application is a section 371 national-stage phase of International Application No. PCT/US2011/063751, filed 7 Dec. 2011, titled "CRYSTALLINE FORMS OF REBAUDIOSIDE B" which claims priority to U.S. Application Ser. No. 61/422,370, filed 13 Dec. 2010, titled "CRYSTALLINE FORMS OF REBAUDIOSIDE B," which are hereby incorporated by reference in their entirety"

FIELD OF THE INVENTION

The present invention relates to methods of producing crystalline rebaudioside B from rebaudioside A. The present invention also relates to three novel crystal polymorphs of rebaudioside B, as well as methods of converting from one crystal polymorph of rebaudioside B to another crystal polymorph of rebaudioside B.

BACKGROUND OF THE INVENTION

The species *Stevia rebaudiana* ("*Stevia*") has been the subject of considerable research and development efforts directed at the purification of certain naturally occurring sweet glycosides of *Stevia* that have potential as non-caloric sweeteners. Sweet glycosides that may be extracted from *Stevia* include the six rebaudiosides (i.e., rebaudioside A to F), stevioside, dulcoside, and sterebins.

In particular, significant commercial interest has been focused on obtaining and purifying rebaudioside A from the *Stevia*. It is currently possible to purchase rebaudioside A at high levels of purity.

SUMMARY OF THE INVENTION

Rebaudioside B is a compound having the following chemical structure:

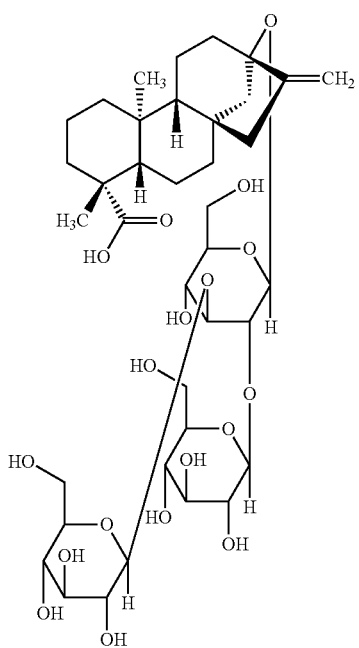

Most commercial interest thus far has been in extraction and purification of rebaudioside A from the *Stevia*. During the extraction of rebaudioside A from *Stevia*, rebaudioside A is separated from other rebaudiosides as well as stevioside, dulcoside, sterebins and other impurities. Though most commercial interest has been in extraction and purification of rebaudioside A, rebaudioside B also has a sweet taste and could be used in certain sweeteners.

Applicants have discovered a commercially useful process for producing crystalline rebaudioside B from rebaudioside A. Applicants have also surprisingly discovered three novel distinct crystal polymorphs of rebaudioside B, as well as methods to convert from one crystal polymorph of rebaudioside B to another. Each crystal polymorph of rebaudioside B has unique dissolution and structural characteristics which may be beneficial in particular commercial applications.

Other objects, features, and advantages of the invention will be apparent from the following detailed description, drawings, and claims.

BRIEF DESCRIPTION OF THE DRAWINGS

FIG. 3 is a table with a peak list of an X-ray diffraction pattern of Form 1

FIG. 7 is a table with a peak list of an X-ray diffraction pattern of Form 2

FIG. 11 is a table with a peak list of an X-ray diffraction pattern of Form 3

FIG. 15 is a table with a peak list of an X-ray diffraction pattern of Form 4

DETAILED DESCRIPTION OF THE INVENTION

Introduction

Figure 1:
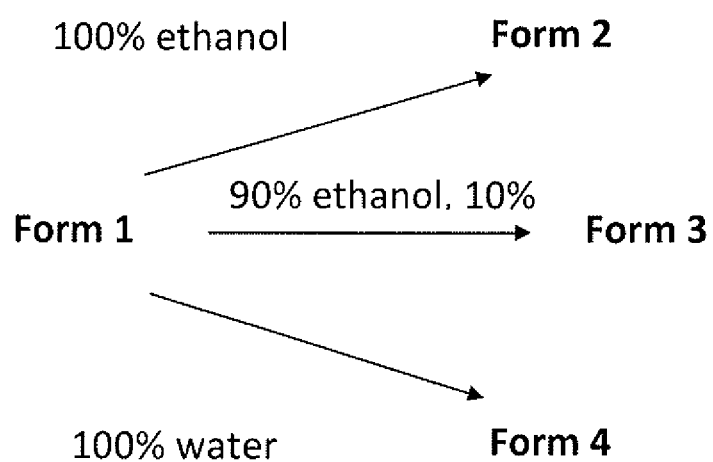
FIG. 1 is a schematic illustrating methods for converting from one crystal polymorph of rebaudioside B to other crystal polymorphs of rebaudioside B in accordance with certain embodiments of this invention.

The present invention provides a process for the production of crystalline rebaudioside B from rebaudioside A. The present invention also relates to three novel and distinct crystal polymorphs of rebaudioside B (described herein as Forms 2, 3, and 4). The present invention also relates to methods for converting from one polymorphic form of rebaudioside B into another polymorphic form of rebaudioside B.

Production of Rebaudioside B from Rebaudioside A

The present invention provides a process for the production of a crystalline form of rebaudioside B from rebaudioside A.

The process for producing a crystalline form of rebaudioside B from rebaudioside A comprises:

(a) providing a rebaudioside A composition;

(b) mixing the rebaudioside A composition with a base and water to yield an alkaline mixture consisting of the rebaudioside A composition, the base, and water;

(c) holding the alkaline mixture for a period of time sufficient to convert a portion of rebaudioside A in the rebaudioside A composition to rebaudioside (d) lowering the pH of the alkaline mixture by adding an acid to the alkaline mixture to yield a pH reduced mixture; and (e) isolating crystalline rebaudioside B from the pH reduced mixture.

Rebaudioside A compositions are commercially available at varying rebaudioside A concentrations. In some embodiments, the rebaudioside A composition for use in the present invention comprises greater than 40% rebaudioside A. In other embodiments, the rebaudioside A composition for use in the present invention comprises greater than 70% rebaudioside A. In yet other embodiments, the rebaudioside A composition comprises greater than 75% rebaudioside A. In yet other embodiments, the rebaudioside A composition comprises greater than 80% rebaudioside A. In yet other embodiments, the rebaudioside A composition comprises greater than 85% rebaudioside A. In yet other embodiments, the rebaudioside A composition comprises greater than 90% rebaudioside A. In yet other embodiments, the rebaudioside A composition comprises greater than 95% rebaudioside A. In yet other embodiments, the rebaudioside A composition comprises greater than 97% rebaudioside A.

In some embodiments, step (h) includes first adding the rebaudioside A composition to water to yield an aqueous mixture, and then adding a base to the aqueous mixture to yield an alkaline mixture. In other embodiments, step (b) includes first adding a base to water to yield an alkaline aqueous solution, and then adding the rebaudioside A composition to the alkaline aqueous solution to yield an alkaline mixture.

The base utilized in step (b) can be any known base including, but not limited to, sodium hydroxide, potassium hydroxide, or calcium hydroxide. Preferably the base is a strong base.

The base utilized in step (b) can be present in the alkaline mixture at any concentration to hydrolyze or convert rebaudioside A to rebaudioside B. In some embodiments, the base can be added at concentrations by weight ranging from 1% to 8% relative to the rebaudioside A composition. In other embodiments, the base can be added at concentrations by weight ranging from 2% to 6% relative to the rebaudioside A composition. In yet other embodiments, the base can be added at a concentration by weight of approximately 4% relative to the rebaudioside A composition.

The alkaline mixture, in step (c), can be held for any length of time to allow sufficient hydrolysis or conversion of rebaudioside A to rebaudioside B. For example, the alkaline mixture can be held for 1, 12, 24, 36, 48, 60, or 72 hours. In some embodiments, the alkaline mixture can held for 8 to 36 hours. In other embodiments, the alkaline mixture can be held for 12 to 24 hours. Generally, as the concentration of the base increases, the amount of holding time of the alkaline mixture necessary for sufficient conversion of rebaudioside A to rebaudioside B decreases.

In some embodiments, the concentration of the rebaudioside A composition in the alkaline mixture can range from 5% to 50%. In other embodiments, the concentration of the rebaudioside A composition in the alkaline mixture can range from 10% to 40%. In yet other embodiments, the concentration of the rebaudioside A composition in the alkaline mixture can range from 15% to 30%. In some embodiments, the alkaline mixture can be an alkaline slurry.

In some embodiments, the alkaline mixture can be held at a high temperature. For example, the alkaline mixture may be maintained at a temperature of greater than 50° C., 60° C., 70° C., 80° C., 90° C., 100° C., or 110° C. The alkaline mixture can be agitated continuously or intermittently.

At the conclusion of step (c) of the process, a significant portion of the rebaudioside A in the rebaudioside A composition will be converted to rebaudioside B.

In step (d) any known organic or inorganic acid may be added to the alkaline mixture to lower the pH of the alkaline mixture, including, but not limited to, citric, acetic, hydrochloric, sulfuric, phosphoric, nitric, or oxalic acids.

The acid is added to the alkaline mixture to bring the pH of the pH reduced mixture in a range of from pH 6 to pH 8, or approximately to a neutral pH of 7. Applicants have discovered that, surprisingly, after addition of acid to neutralize the mixture, the rebaudioside B crystallized (in Form 1) and precipitated out of solution.

Applicants had attempted to precipitate the rebaudioside B using some conventional methods such as cooling the alkaline mixture. These attempts did not prove successful. Applicants, however, unexpectedly discovered that addition of an acid at this point in the process caused the precipitation of a polymorphic form of crystalline rebaudioside B (Form 1).

In some embodiments, the acid addition can occur at elevated temperatures. As such, in embodiments where the alkaline mixture is held at high temperatures, there may be no need to reduce the temperatures at which the alkaline mixture is held prior to addition of the acid. In some embodiments, the acid addition can occur at the same elevated temperature as the alkaline mixture. The ability to avoid temperature reduction can be commercially significant.

After precipitation of crystalline rebaudioside B, the resulting rebaudioside B crystal polymorph can be isolated by conventional filtering processes, for example using a Buchner funnel. In a production environment isolation may take place, for example, by centrifugation, pannevis filtration, nutch, Rosemund, or the like. The isolated crystalline rebaudioside B product can be dried by exposure to a nitrogen stream and/or exposure to heat and/or exposure to vacuum (e.g. vacuum oven). In some embodiments, isolation of the resulting rebaudioside B crystal polymorph can occur at elevated temperatures. In some embodiments, steps (c), (d), and (e) can all occur at elevated temperatures.

The process described above yields a substantially pure resulting crystalline rebaudioside B product. In some embodiments, the resulting crystalline rebaudioside B has a purity of greater than 80% by weight, greater than 85% by weight, greater than 90% by weight, greater than 95% by weight, greater than 97% by weight, or greater than 99% by weight.

Figure 2:
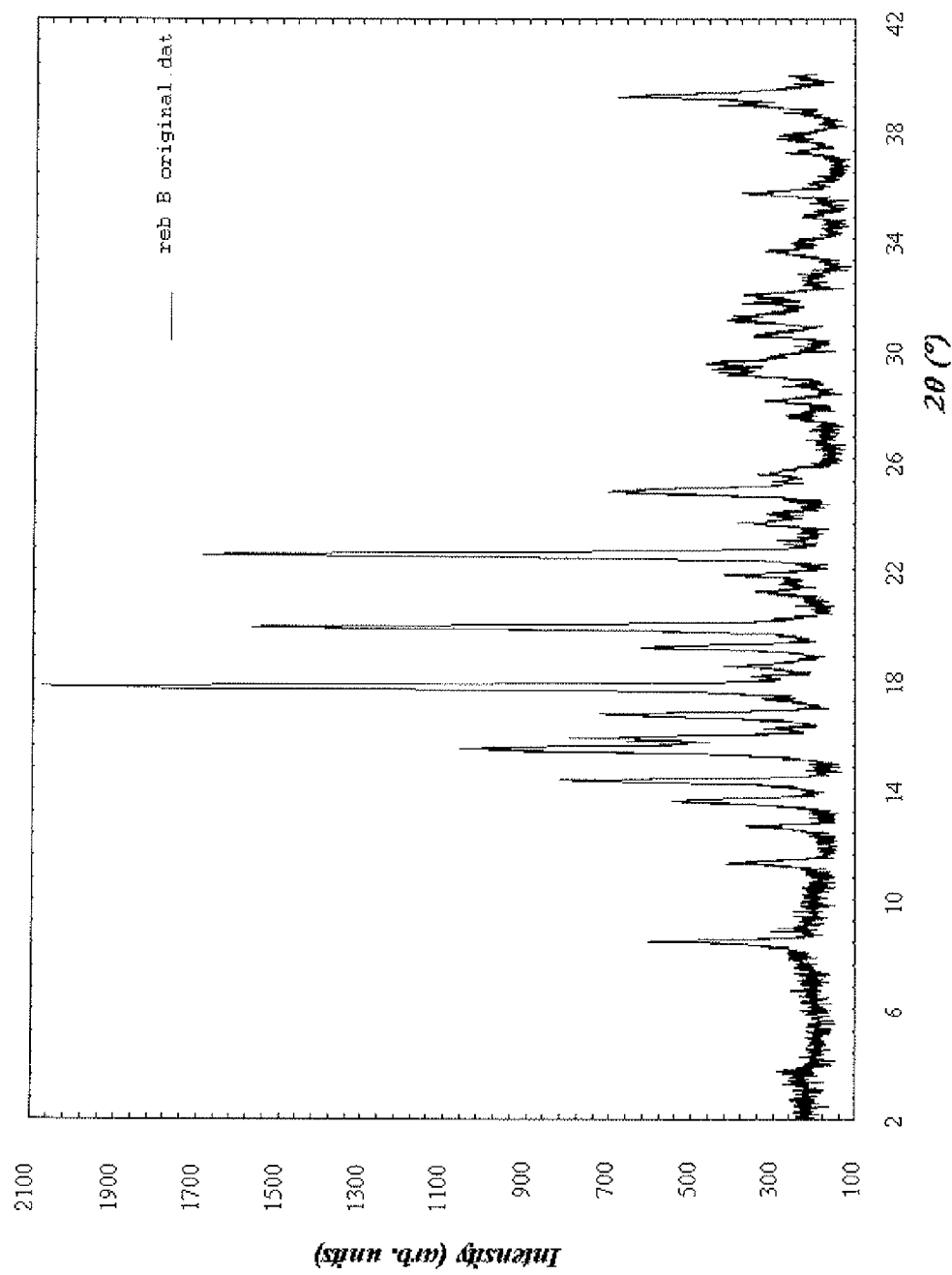
FIG. 2 is a powder X-ray diffraction pattern of Form 1
Figure 4:
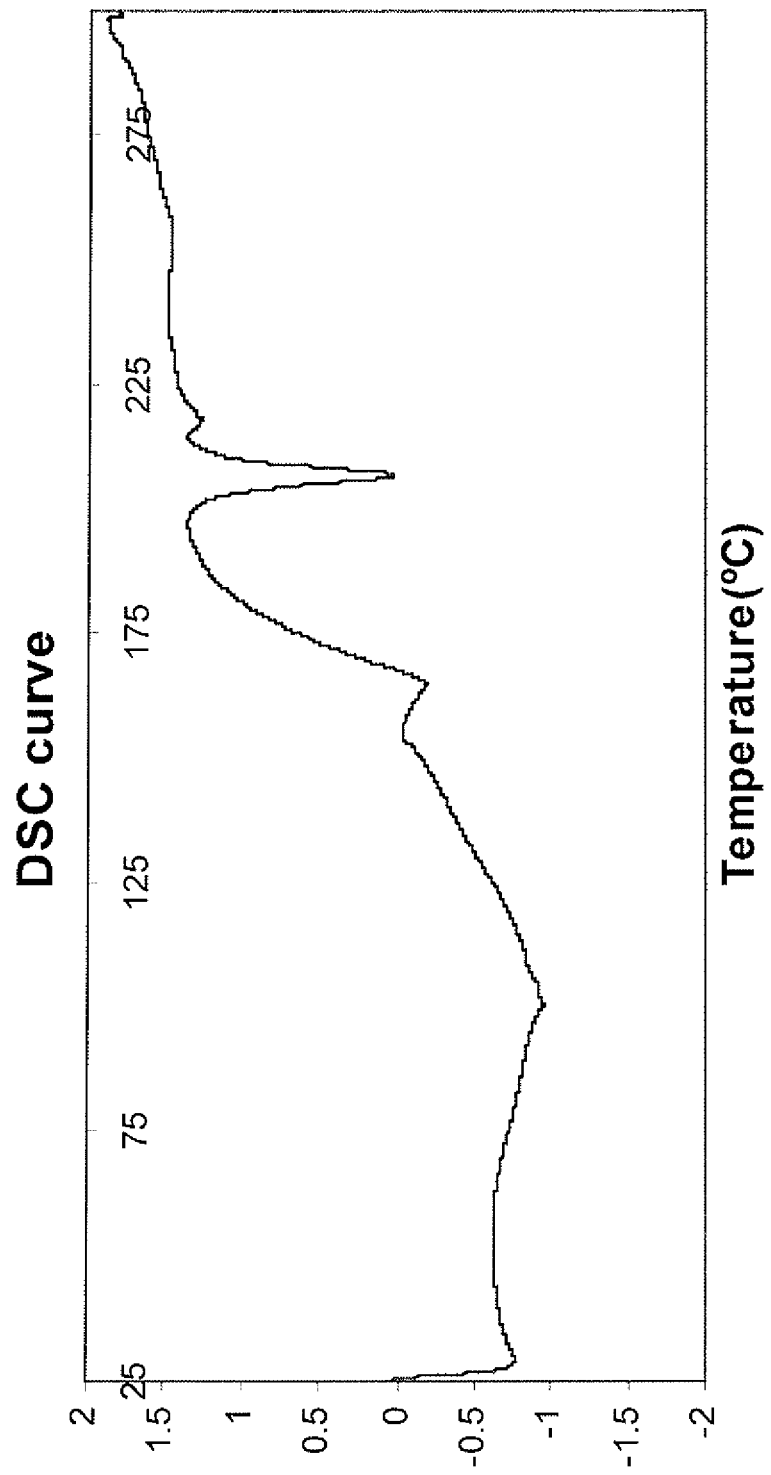
FIG. 4 is a DSC pattern of Form 1
Figure 5:
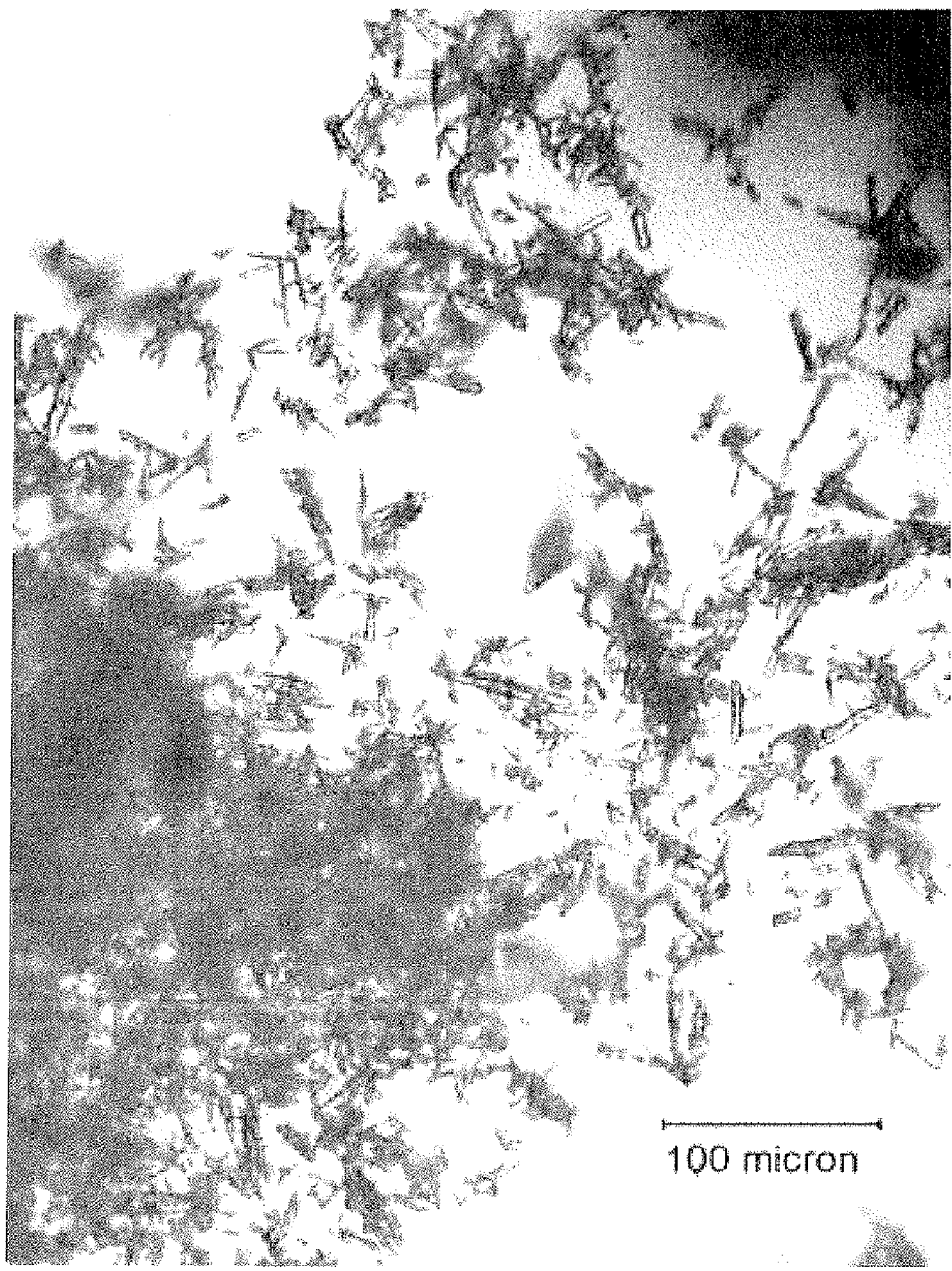
FIG. 5 is a microscopic image of Form 1

This crystalline rebaudioside B product obtained from the process is present in Form 1 having an X-ray diffraction pattern that is substantially similar to the X-ray diffraction pattern shown in FIG. 2.

Crystal Polymorphs of Rebaudioside B

Applicants have surprisingly discovered three distinct and novel crystal polymorphs of rebaudioside B: Form 2, Form 3, and Form 4. Polymorphism is defined as the ability of a substance to exist in two or more crystalline states that have different arrangements and/or conformations of the molecules in the crystal lattice. Polymorphism may cause physical properties such as density, melting point, and rate of dissolution to change.

Four crystal polymorphs of rebaudioside B (Form 1, Form 2, Form 3, and Form 4) were characterized by their X-ray powder diffraction patterns. The powder X-ray diffraction patterns were measured on a Rigaku Miniflex diffractometer with CuK radiation ($\lambda$=1.54 Å). Characteristic peaks typically have a peak position that varies about +/−0.2. For example, the presence of a peak at 4.8 may be satisfied by the presence of a peak in the range of 4.6 to 5.0.

To prepare the X-ray powder diffraction pattern samples, a sample of the composition was ground into a fine powder using a mortar and pestle. The fine powder was then packed into an aluminum sample holder with a zero background silicon plate. The samples were obtained using a Rigaku Miniflex diffractometer with CuK radiation ($\lambda$=1.54 Å). The scan speed was run at 0.2 degrees per minute.

The solubility of each of the four crystal polymorphs of rebaudioside B was determined in the following manner. Experiments were conducted using a known volume of solvent in a temperature controlled stirred vessel. The amount of solvent used was either 1 mL or 2 mL. Rebaudioside B was added to the solvent in the temperature controlled stirred vessel in 0.5 mg increments and held to visually determine if it dissolved. If the first 0.5 mg increment dissolved, another 0.5 mg increment was added and again held to visually determine if it dissolved. This procedure was continued until the material would not dissolve or until crystalline material started coming out of solution, indicating that a crystalline transformation had occurred. Each incremental addition of rebaudioside B was allowed a maximum of 1 hour to dissolve (if dissolution took place more quickly it was not necessary to wait the full 1 hour). Each trial was ended if dissolution did not occur within 1 hour or if conversion to a different form occurred.

Form 1

The crystalline structure of Form 1 of rebaudioside B can be characterized in displaying two or more characteristic X-ray diffraction peaks as identified in TABLE 1. The crystalline structure of Form 1 can also characterized in displaying 2 or more, 3 or more, 4 or more, 5 or more, 6 or more, 7 or more, 8 or more, 9 or more, 10 or more, 11 or more, 12 or more, 13 or more, or all 14 of the characteristic peaks.

TABLE 1

Characteristic X-ray Diffraction Peaks of Form 1

| Peak Position (2θ) ($\lambda$ = 1.54 Å) | Intensity I/Io (%) |
|---|---|
| 8.5 | 29 |
| 13.5 | 26 |
| 19.9 | 75 |
| 21.1 | 17 |
| 29.1 | 20 |
| 29.3 | 23 |
| 29.5 | 24 |
| 31.7 | 18 |
| 32.0 | 18 |
| 33.6 | 16 |
| 35.7 | 18 |
| 37.2 | 14 |
| 37.7 | 14 |
| 39.2 | 33 |

Form 1 can be characterized by having a powder X-ray diffraction pattern that is substantially similar to the X-ray diffraction pattern shown in FIG. 2. By substantially similar it is meant that the X-ray diffraction pattern of a particular form of rebaudioside B crystal that displays a pattern of peaks that is similar in peak position and intensity such that one of skill in the art of X-ray diffraction pattern interpretation would conclude that the compounds have the same composition and crystal structure.

Form 1 rebaudioside B can have a powder X-ray diffraction pattern containing at least one of the following peaks: 8.5, 13.5, 29.3, 32.0, or 39.2. Form 1 rebaudioside B can also have a powder X-ray diffraction pattern containing the following peaks: 8.5 and 13.5. Form 1 rebaudioside B can also have a powder X-ray diffraction pattern containing the following peaks: 8.5 and 29.3. Form 1 rebaudioside B can also have a powder X-ray diffraction pattern containing the following peaks: 13.5 and 39.2. Form 1 rebaudioside B can also have a powder X-ray diffraction pattern containing the following peaks: 13.5 and 32.0. Form 1 rebaudioside B can also have a powder X-ray diffraction pattern containing the following peaks: 8.5, 29.3, and 39.2. Form 1 rebaudioside B can also have a powder X-ray diffraction pattern containing the following peaks: 8.5, 13.5, and 39.2. Form 1 rebaudioside B can also have a powder X-ray diffraction pattern containing the following peaks: 8.5, 13.5, 29.3, 32.0, and 39.2.

Form 1 is the crystalline form of rebaudioside B produced by the process of the present invention for production of crystalline rebaudioside B from rebaudioside A.

Form 1 of rebaudioside B is characterized as having low solubility in water, moderate solubility in ethanol, and high solubility in an ethanol/water mixture. Form 1 can be characterized by having a solubility in water at 25° C. of less than about 0.5 (mg/mL water).

Form 1 can be characterized by having a solubility in a 95% ethanol/5% water solution at 25° C. ranging from 24 to 32 (mg/mL 95% ethanol/5% water solution). Form 1 can also be characterized by having a solubility in a 95% ethanol/5% water solution at 25° C. ranging from 26 to 30 (mg/ml, 95% ethanol/5% water solution). Form 1 can also be characterized by having a solubility in a 95% ethanol/5% water solution at 25° C. of about 28 (mg Form 1/mL 95% ethanol/5% water solution).

Form 1 can also be characterized by having a solubility in ethanol at 25° C. ranging from 6 to 10 (mg/mL ethanol). Form 1 can also be characterized by having a solubility in ethanol at 25° C. ranging from 7 to 9 (mg/mL ethanol). Form 1 can also be characterized by having a solubility in ethanol at 25° C. of about 8.3 (mg/mL ethanol).

Form 2

In some embodiments, the crystalline structure of Form 2 of rebaudioside B is characterized in displaying two or more characteristic X-ray diffraction peaks as identified in TABLE 2. In other embodiments, the crystalline structure of Form 2 is characterized in displaying 2 or more, 3 or more, 4 or more, 5 or more, 6 or more, 7 or more, 8 or more, 9 or more, 10 or more, 11 or more, or all 12 of the characteristic peaks.

TABLE 2

Characteristic X-ray Diffraction Peaks of Form 2

| Peak Position (2θ) ($\lambda$ = 1.54 Å) | Intensity I/Io (%) |
|---|---|
| 5.1 | 100 |
| 6.7 | 41 |
| 9.2 | 31 |
| 10.3 | 16 |
| 12.1 | 60 |
| 13.1 | 31 |
| 16.2 | 63 |
| 16.9 | 52 |
| 18.2 | 50 |
| 19.5 | 66 |
| 22.2 | 74 |
| 27.0 | 30 |

Figure 6:
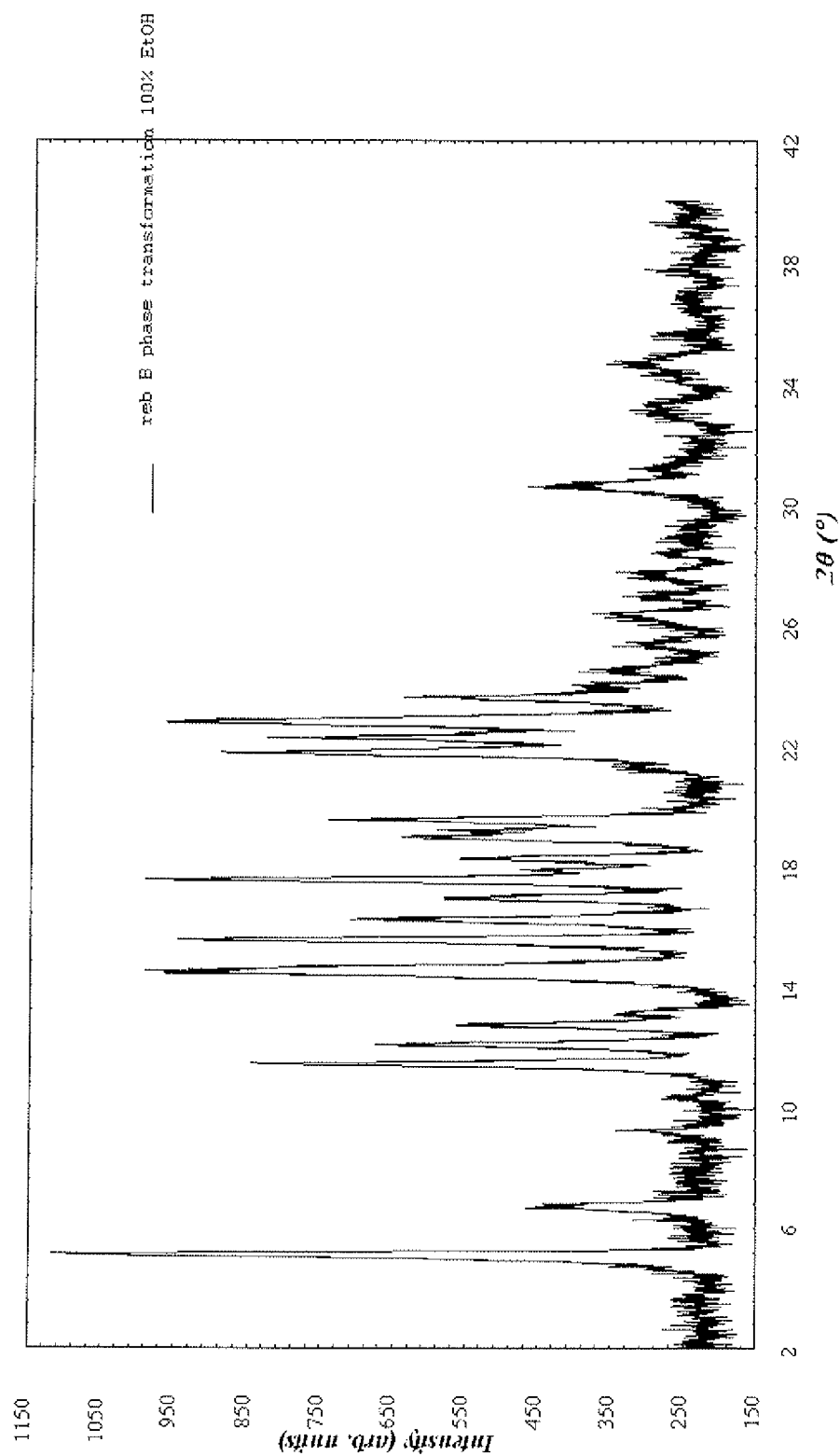
FIG. 6 is a powder X-ray diffraction pattern of Form 2
Figure 8:
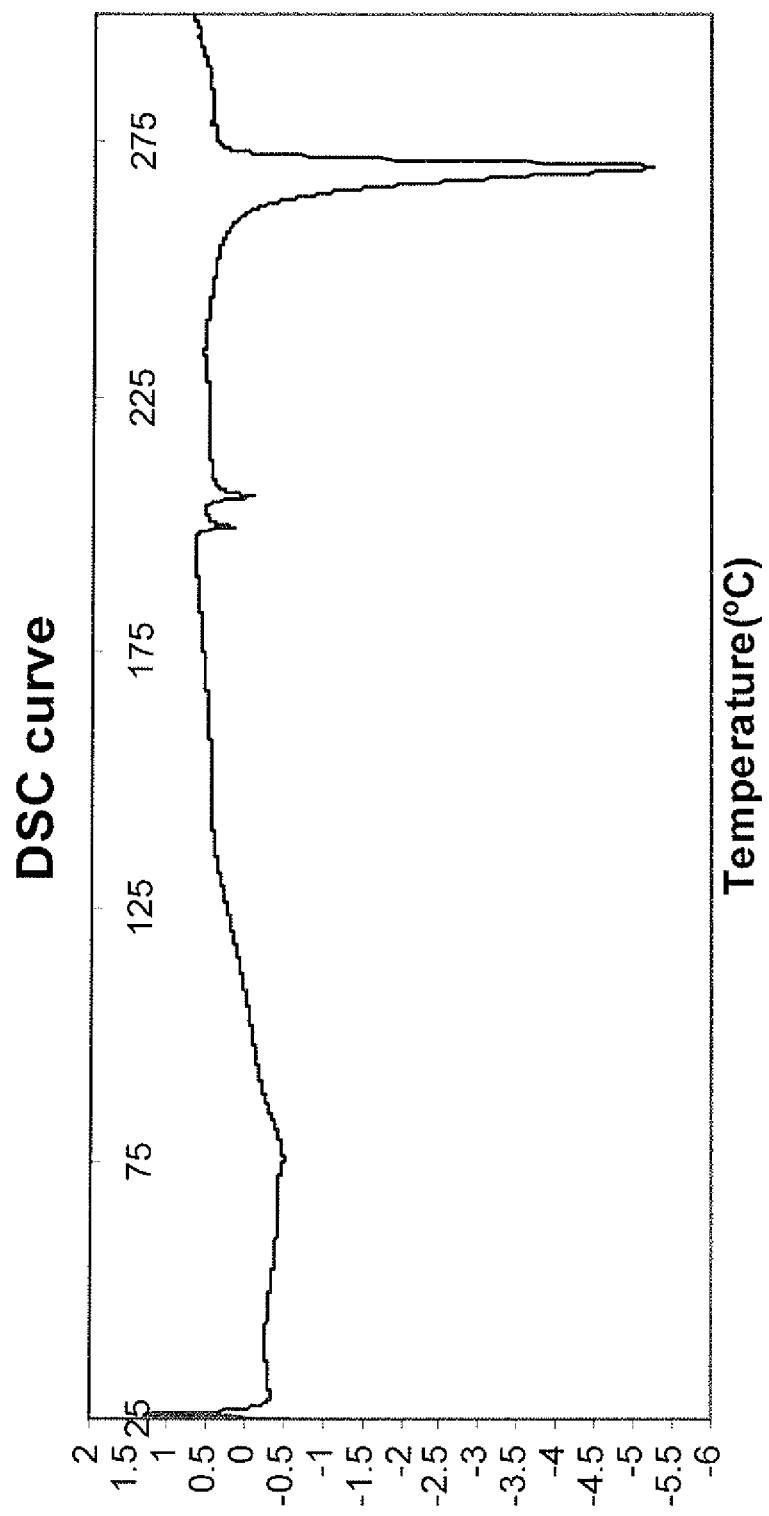
FIG. 8 is a DSC pattern of Form 2
Figure 9:
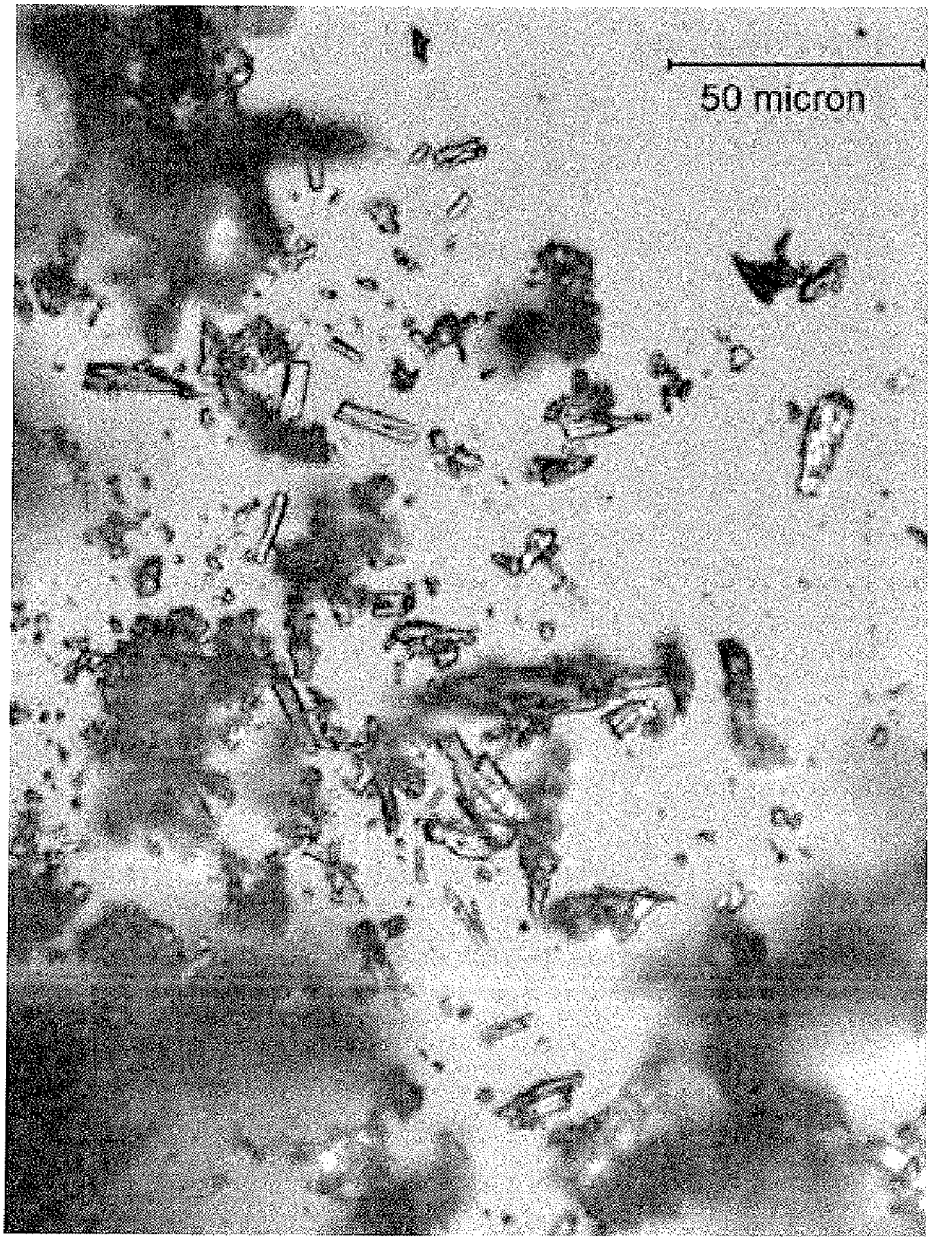
FIG. 9 is a microscopic image of Form 2

In some embodiments, Form 2 can be characterized by having a powder X-ray diffraction pattern that is substantially similar to the X-ray diffraction pattern shown in FIG. 6.

In one particular embodiment, Form 2 rebaudioside B has a powder X-ray diffraction pattern containing at least one of the following peaks: 5.1, 6.7, 9.2, 10.3, or 12.1. In another particular embodiment, Form 2 rebaudioside B has a powder X-ray diffraction pattern containing the following peaks: 5.1 and 6.7. In yet another particular embodiment, Form 2 rebaudioside B has a powder X-ray diffraction pattern containing the following peaks: 5.1 and 9.2. In yet another particular embodiment, Form 2 rebaudioside B has a powder X-ray diffraction pattern containing the following peaks: 6.7 and 10.3. In yet another particular embodiment, Form 2 rebaudioside B has a powder X-ray diffraction pattern containing the following peaks: 5.1, 6.7, and 12.1. In yet another particular embodiment, Form 2 rebaudioside B has a powder X-ray diffraction pattern containing the following peaks: 6.7, 10.3, and 12.1. In yet another particular embodiment, Form 2 rebaudioside B has a powder X-ray diffraction pattern containing the following peaks: 5.1, 6.7, 9.2, 10.3, and 12.1.

Form 2 of rebaudioside B is characterized as having low solubility in water and a low solubility in ethanol. In some embodiments, Form 2 is characterized by having a solubility in water at 25° C. of less than about 0.5 (mg/mL water).

In some embodiments, Form 2 is characterized by having a solubility in ethanol at 25° C. ranging from 1 to 5 (mg/mL ethanol). In other embodiments, Form 2 is characterized by having a solubility in ethanol at 25° C. ranging from 2 to 4 (mg/mL ethanol). In yet other embodiments, Form 2 is characterized by having a solubility in ethanol at 25° C. of about 2.7 (mg/mL ethanol).

Form 3

In some embodiments, the crystalline structure of Form 3 of rebaudioside B is characterized in displaying two or more characteristic X-ray diffraction peaks as identified in TABLE 3. In other embodiments, the crystalline structure of Form 3 is characterized in displaying 3 or more, 4 or more, or all 5 of the characteristic peaks.

TABLE 3

Characteristic X-ray Diffraction Peaks of Form 3

| Peak Position (2θ) (λ = 1.54 Å) | Intensity I/Io (%) |
|---|---|
| 4.8 | 100 |
| 6.4 | 31 |
| 8.9 | 9 |
| 17.3 | 28 |
| 23.3 | 8 |

Figure 10:
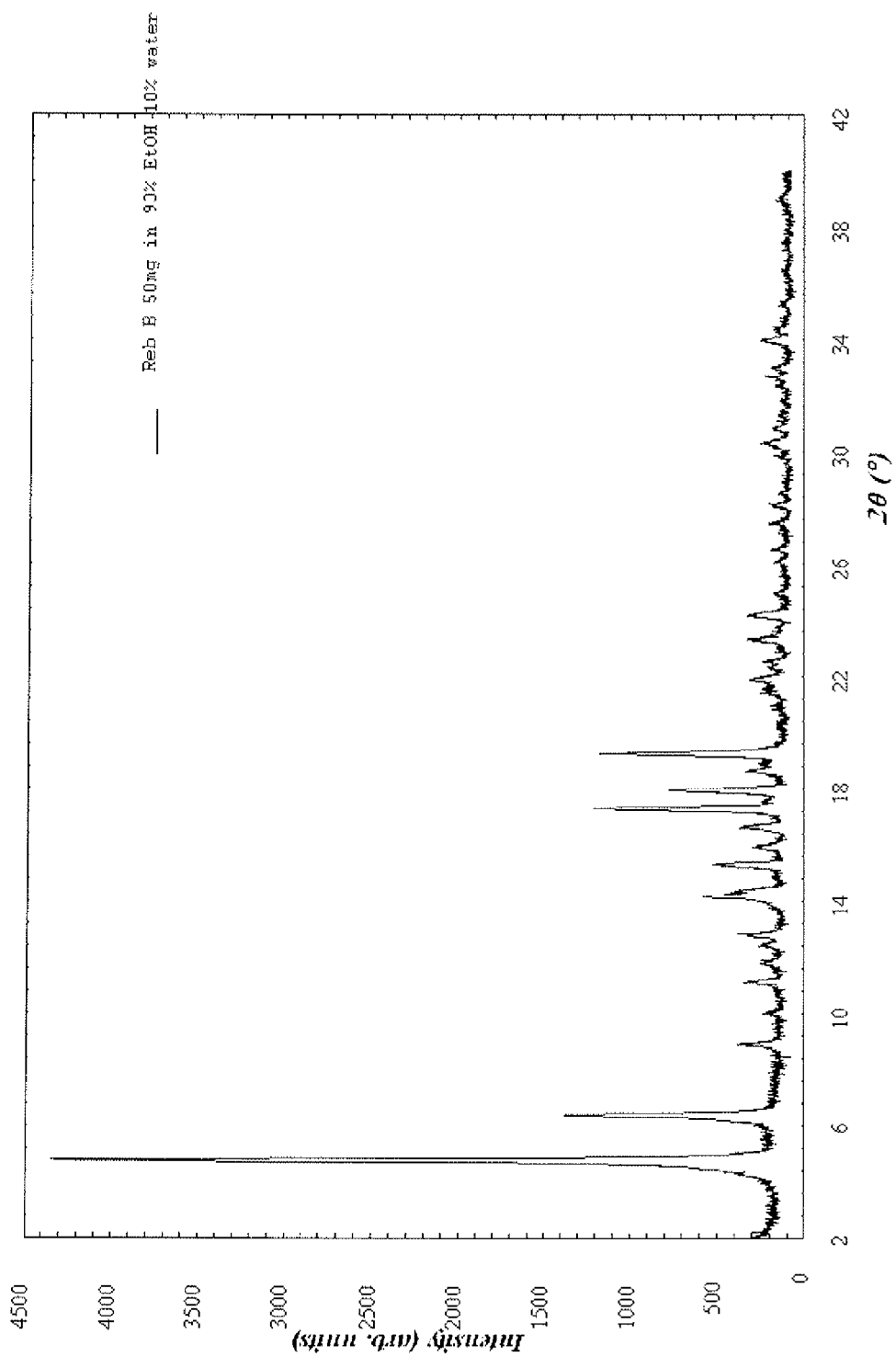
FIG. 10 is a powder X-ray diffraction pattern of Form 3
Figure 12:
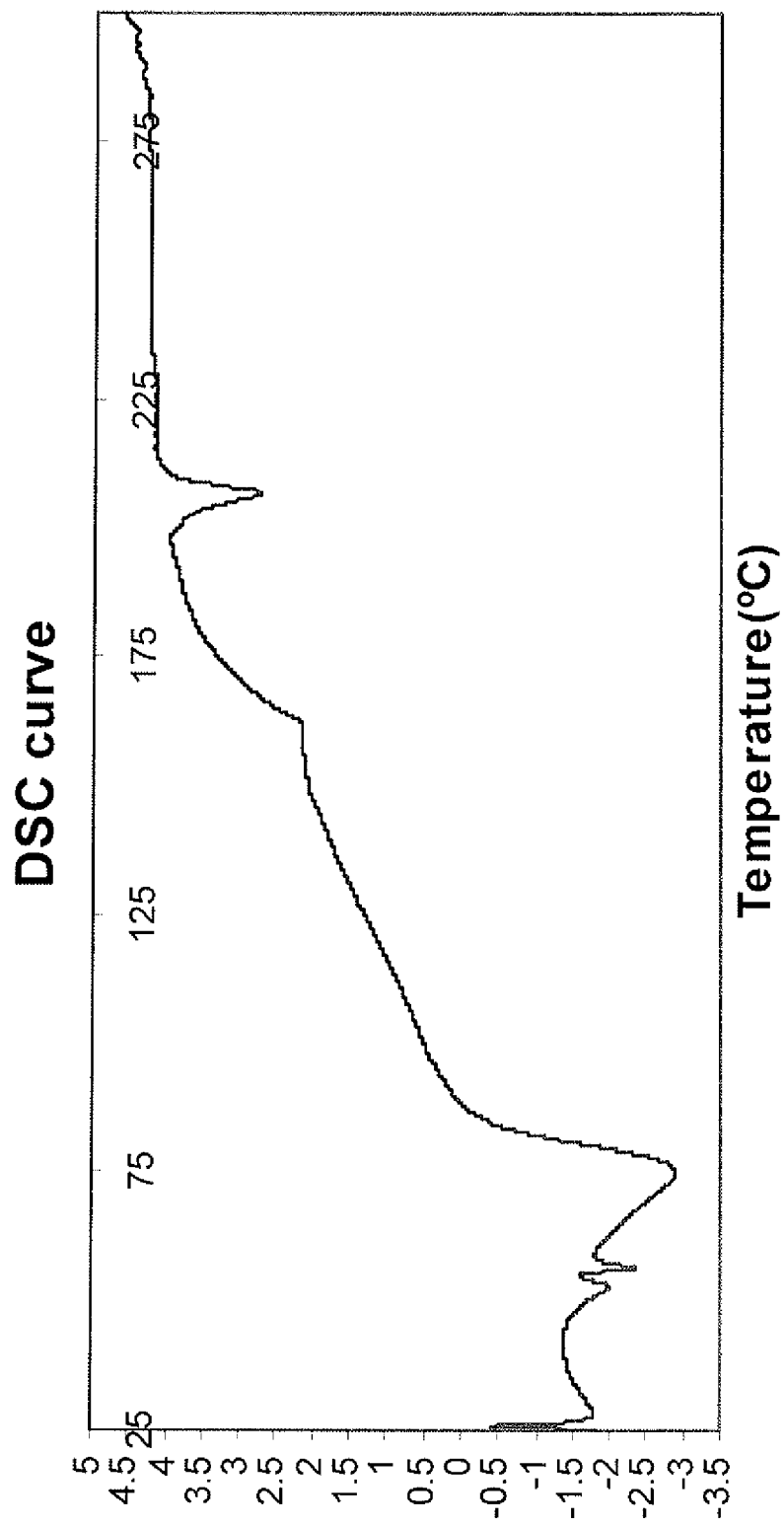
FIG. 12 is a DSC pattern of Form 3
Figure 13:
FIG. 13 is a microscopic image of Form 3

In other embodiments, Form 3 can be characterized by having a powder X-ray diffraction pattern that is substantially similar to the X-ray diffraction pattern shown in FIG. 10.

In one particular embodiment, Form 3 rebaudioside B has a powder X-ray diffraction pattern containing at least one of the following peaks: 4.8, 6.4, 8.9, or 17.3. In another particular embodiment, Form 3 rebaudioside B has a powder X-ray diffraction pattern containing the following peaks: 4.8 and 6.4. In yet another particular embodiment, Form 3 rebaudioside B has a powder X-ray diffraction pattern containing the following peaks: 4.8 and 8.9. In yet another particular embodiment, Form 3 rebaudioside B has a powder X-ray diffraction pattern containing the following peaks: 6.4 and 17.3. In yet another particular embodiment, Form 3 rebaudioside B has a powder X-ray diffraction pattern containing the following peaks: 6.4, and 8.9. In yet another particular embodiment, Form 3 rebaudioside B has a powder X-ray diffraction pattern containing the following peaks: 4.8, 6.4, 8.9, and 17.3.

Form 3 of rebaudioside B is characterized as having low solubility in water and a moderate solubility in ethanol. In some embodiments, Form 3 is characterized by having a solubility in water at 25° C. of less than about 0.5 (mg/mL water).

In some embodiments, Form 3 is characterized by having a solubility in ethanol at 25° C. ranging from 6 to 14 (mg/mL ethanol). In other embodiments, Form 3 is characterized by having a solubility in ethanol at 25° C. ranging from 8 to 12 (mg/mL ethanol). In yet other embodiments, Form 3 is characterized by having a solubility in ethanol at 25° C. of about 10 (mg/mL ethanol).

Form 4

The crystalline structure of Form 4 of rebaudioside B is characterized in displaying two or more characteristic X-ray diffraction peaks as identified in TABLE 4. In other embodiments, the crystalline structure of Form 4 is characterized in displaying all 3 of the characteristic peaks.

TABLE 4

Characteristic X-ray Diffraction Peaks of Form 4

| Peak Position (2θ) (λ = 1.54 Å) | Intensity I/Io (%) |
|---|---|
| 3.6 | 100 |
| 7.5 | 7 |
| 15.1 | 28 |

Figure 14:
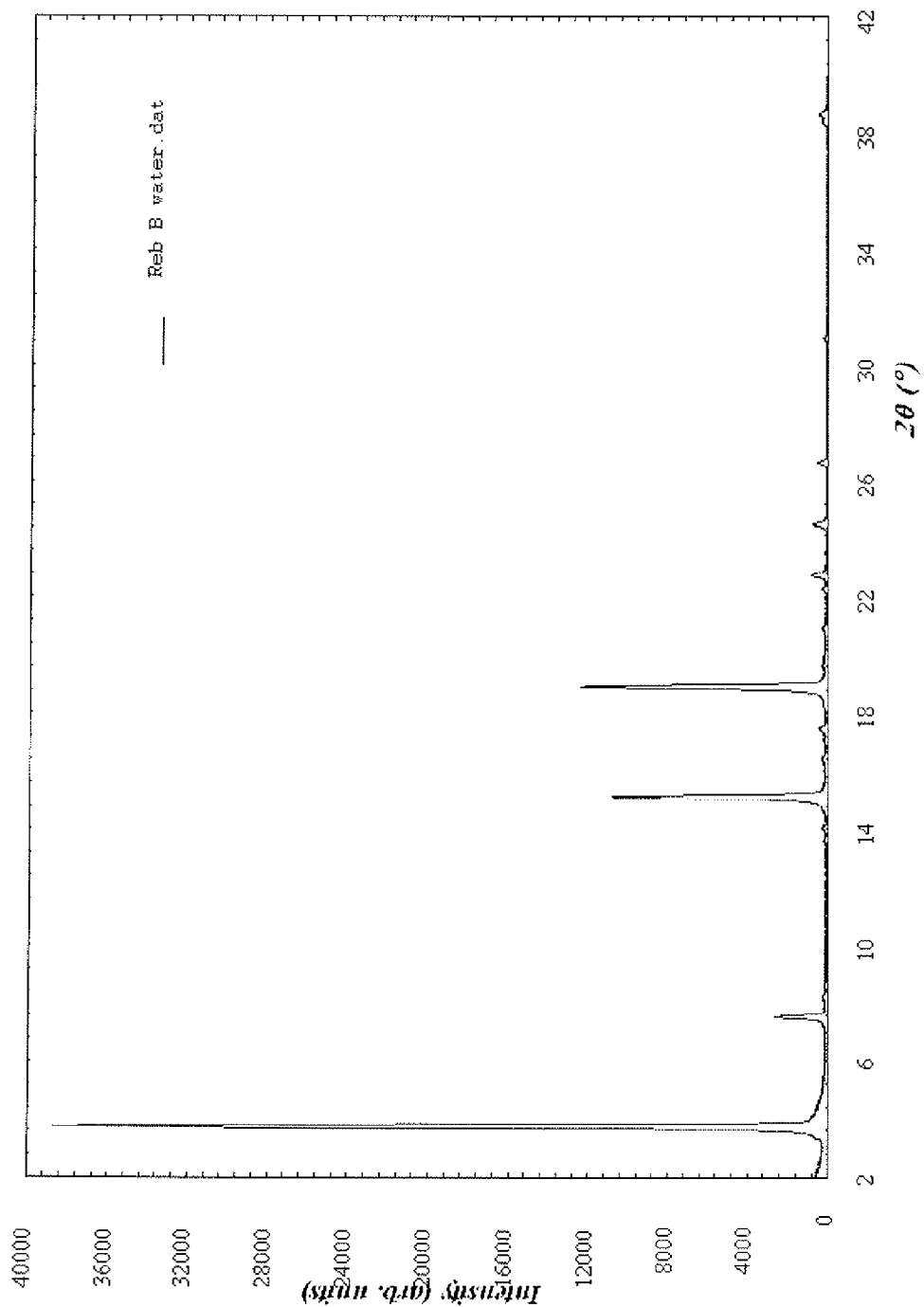
FIG. 14 is a powder X-ray diffraction pattern of Form 4
Figure 16:
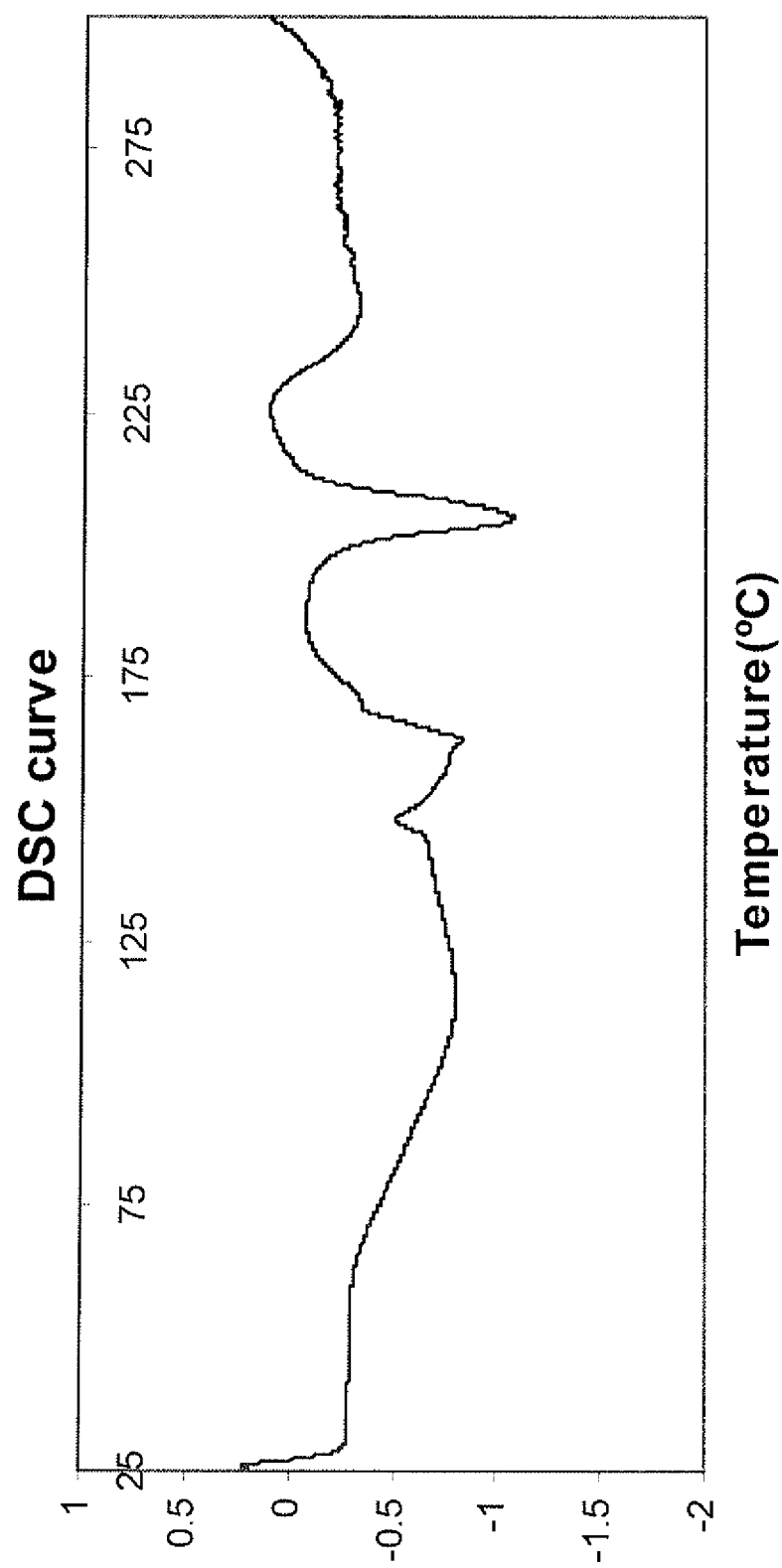
FIG. 16 is a DSC pattern of Form 4
Figure 17:
FIG. 17 is a microscopic image of Form 4

In other embodiments, Form 4 can be characterized by having a powder X-ray diffraction pattern that is substantially similar to the X-ray diffraction pattern shown in FIG. 14.

In one particular embodiment, Form 4 rebaudioside 13 has a powder X-ray diffraction pattern containing at least one of the following peaks: 3.6, 7.5, or 15.1. In another particular embodiment, Form 4 rebaudioside B has a powder X-ray diffraction pattern containing the following peaks: 3.6 and 7.5. In yet another particular embodiment, Form 4 rebaudioside B has a powder X-ray diffraction pattern containing the following peaks: 3.6 and 15.1. In yet another particular embodiment, Form 4 rebaudioside B has a powder X-ray diffraction pattern containing the following peaks: 7.5 and 15.1. In yet another particular embodiment, Form 4 rebaudioside B has a powder X-ray diffraction pattern containing the following peaks: 3.6, 7.5 and 15.1.

Conversion Between Different Polymorphic Forms of Rebaudioside B

Applicants have discovered methods for converting from one particular crystal polymorph of rebaudioside B to another. These other crystal polymorphs of rebaudioside B have different properties from one another which may prove useful in different commercial circumstances.

Conversion from Form 1 to Form 2

Form 1 can be treated in order to convert at least a portion of Form 1 into Form 2. Form 1 can be converted to Form 2 by suspension in pure ethanol. The suspension can be heated to a temperature ranging from 40° C. to 80° C. In some embodiments, the suspension can be heated to a temperature ranging from 50° C. to 70° C. In other embodiments, the suspension can be heated to a temperature of approximately 60° C.

Form 1 can be suspended in pure ethanol for a period of time sufficient for conversion of a portion of Form 1 to Form 2. In some embodiments, Form 1 can be suspended in pure ethanol for a period of time of from 1 minute to 10 hours. In other embodiments, Form 1 can be suspended in pure ethanol for a period of time of from 1 to 4 hours. The suspension can be stirred continuously or intermittently. Stirring the suspension can cause the conversion to Form 2 to occur more quickly.

After Form 1 has converted to Form 2, the Form 2 crystal polymorph of rebaudioside B can be isolated by conventional filtering processes, for example using a Buchner funnel. In a production environment isolation may take place, for example, by centrifugation, pannevis filtration, nutch, Rosemund, or the like. The Form 2 crystal polymorph of rebaudioside B product can be dried by exposure to a nitrogen stream and/or exposure to heat and/or exposure to vacuum (e.g. vacuum oven).

Conversion from Form 1 to Form 3

Form 1 can be treated in order to convert at least a portion of Form 1 into Form 3. Form 1 can be converted to Form 3 by suspension in an ethanol and water solution. In some embodiments, the concentration of ethanol in the solution can range from 70% to 97% and the concentration of water in the solution can range from 3% to 30%. In other embodiments, the concentration of ethanol in the solution can range from 85% to 95% and the concentration of water in the solution can range from 5% to 15%. In a particular embodiment, the concentration of ethanol in the solution is approximately 95% and the concentration of water in the solution is approximately 5%. In another particular embodiment, the concentration of ethanol in the solution is approximately 90% and the concentration of water in the solution is approximately 10%.

The suspension (Form 1 in an ethanol and water solution) can be heated to a temperature ranging from 40° C. to 80° C. In some embodiments, the suspension can be heated to a temperature ranging from 50° C. to 70° C. In other embodiments, the suspension can be heated to a temperature of approximately 60° C.

Form 1 can be suspended in in an ethanol and water solution for a period of time sufficient for conversion of a portion of Form 1 to Form 3. In some embodiments, Form 1 can be suspended in an ethanol and water solution for a period of time of from 1 minute to 10 hours. In other embodiments, Form 1 can be suspended in an ethanol and water solution for a period of time of from 1 to 4 hours. The suspension can be stirred continuously or intermittently.

After Form 1 has converted to Form 3, the Form 3 crystal polymorph of rebaudioside B can be isolated by conventional filtering processes, for example using a Buchner funnel. In a production environment isolation may take place, for example, by centrifugation, pannevis filtration, nutch, Rosemund, or the like. The Form 3 crystal polymorph of rebaudioside B product can be dried by exposure to a nitrogen stream and/or exposure to heat and/or exposure to vacuum (e.g. vacuum oven).

Conversion from Form 1 to Form 4

Form 1 can be treated in order to convert at least a portion of Form 1 into Form 4. Form 1 can be converted to Form 4 by suspension in water. The water can be held at room temperature.

Form 1 can be suspended in water for a period of time sufficient for conversion of a portion of Form 1 to Form 4. In some embodiments, Form 1 can be suspended in water for a period of time of from 1 minute to 40 hours. In other embodiments, Form 1 can be suspended in water for a period of time of from 10 to 30 hours. The suspension can be stirred continuously or intermittently. Preferably, the suspension is stirred lightly.

After Form 1 has converted to Form 4, the Form 4 crystal polymorph of rebaudioside B can be isolated by conventional filtering processes, for example using a Buchner funnel. In a production environment isolation may take place, for example, by centrifugation, pannevis filtration, nutch, Rosemund, or the like. The Form 4 crystal polymorph of rebaudioside B product can be dried by exposure to a nitrogen stream and/or exposure to heat and/or exposure to vacuum (e.g. vacuum oven).

EXAMPLES

Examples 1a, 1b, and 1c

Production of Crystalline Rebaudioside B from Rebaudioside A

Example 1a

A rebaudioside A composition was obtained from Cargill, Incorporated. This starting rebaudioside A composition comprised 98.7% rebaudioside A. The starting composition also included small quantities of rebaudioside B (1.1%) as well as other glycosides.

100 grams of the rebaudioside A composition, 400 grams of DI water, and a stir bar were added to a three neck 1000 mL round bottom flask. The flask was heated to 95° C. and monitored using a thermometer through one of the necks of the flask. When the temperature reached 95° C., 4.05 grams of sodium hydroxide (NaOH) were added to the solution in the flask.

After 24 hours, the solution had turned a dark brown color. After 72 hours, no precipitate had formed in the flask. Samples were extracted from the flask at times: 24 hours, 48 hours, and 72 hours after NaOH addition. Analysis of these samples can be seen in TABLE 5 below. After 72 hours, two aliquots of 1 gram each of citric acid were added to the solution in the flask. After the second aliquot, the pH of the solution was approximately 7. The temperature was maintained at 95° C.

A precipitant then started to form in the flask. After 4 hours the mixture in the flask was filtered using a Buchner funnel with #41 Whatman filter paper. The mixture filtered fairly slowly. A sample was taken from the filtrate. Analysis of this filtrate sample can be seen in TABLE 5 below.

The retentate was then washed with two aliquots of water each matching the weight of the wet retentate (approximately 64 grams). The brown color was removed from the retenate after the two washings. A sample was taken from the wash filtrate. Analysis of this wash filtrate sample can be seen in TABLE 5 below.

The retentate was then transferred to a tin and dried under vacuum for 2 days. The dried product weighed 26.98 grams. As seen in TABLE 5, this dried product had a purity of 98.4% rebaudioside B. This resulting crystalline rebaudioside B composition had an X-ray diffraction pattern substantially similar to that of FIG. 2 (Form 1).

TABLE 5

| Sample | % rebaudioside B | % rebaudioside A |
|---|---|---|
| 24 hours after NaOH addition | 79.6 | 19.5 |
| 48 hours after NaOH addition | 82.3 | 16.8 |
| 72 hours after NaOH addition | 85.3 | 13.7 |
| Filtrate | 78.7 | 20.1 |
| Wash Filtrate | 76.9 | 21.7 |
| Dried Product | 98.4 | 1.3 |

Compositional analysis of materials in TABLE 5 was done by HPLC on a Synergi 4u Hydro-RP 80A, 250×4.60 mm, 4 micron Batch no. 487909-3 with 75:25 acetic acid in water pH 3.3: Acetonitrile solution as the diluents, with UV detection at 210 nm.

Example 1b

A rebaudioside A composition was obtained from Cargill, Incorporated. This starting rebaudioside A composition comprised 98.7% rebaudioside A. The starting composition also included small quantities of rebaudioside B (1.1%) as well as other glycosides.

A five liter crystallizer with baffles and agitator was obtained from Chemglass. The crystallizer was filled with 4000 grams of distilled water and heated to 90° C. with a water bath. Once the water in the crystallizer reached 90° C., 1000 grams of the rebaudioside A composition was added to the crystallizer.

After the rebaudioside A composition was dissolved, 41.36 grams of sodium hydroxide (NaOH) was added to the crystallizer. Ten minutes after the NaOH was added, the solution in the crystallizer had turned brown. The solution was allowed to remain in the crystallizer for 72 hours.

After 72 hours, 20 grams of food grade citric acid was added to the solution in the crystallizer. A precipitant began to form almost instantly. The mixture was allowed to remain in the crystallizer at 90° C. for an additional 24 hours.

A Rosenmund filter with a 20 micron stainless steel screen was obtained. The filter was preheated to 90° C. The mixture was then loaded from the crystallizer onto the filter. Filtering was started with 0.5 bar of $N_2$ pressure. After 15 minutes the $N_2$ pressure was increased to 1 bar. A sample was taken from the filtrate. Analysis of this filtrate sample can be seen in TABLE 6 below.

After filtration, the retentate was washed with 2 aliquots of 400 mL DI water each. A sample was taken from each wash filtrate. Analysis of each wash filtrate sample can be seen in TABLE 6 below. The retentate was dried in the filter at 90° C. with 6 liters per minute of $N_2$ sparge from the bottom of the unit, and with 22 inches of mercury vacuum. After one hour, the temperature was increased to 105° C. The product was dry after 9 hours of total drying time. The dried product weighed 154.6 grams. As seen in TABLE 6, this dried product had a purity of 96.28% rebaudioside B. This resulting crystalline rebaudioside B composition had an X-ray diffraction pattern substantially similar to that of FIG. 2 (Form 1).

TABLE 6

| Sample | % rebaudioside A | % rebaudioside B |
|---|---|---|
| Dried Product | 0.88 | 96.28 |
| Filtrate | 19.66 | 78.46 |
| First Wash Filtrate | 18.27 | 79.32 |
| Second Wash Filtrate | 20.86 | 79.14 |

Compositional analysis of materials in TABLE 6 was done by HPLC on a Synergi 4u Hydro-RP 80A, 250×4.60 mm, 4 micron Batch no. 487909-3 with 75:25 acetic acid in water pH 3.3: Acetonitrile solution as the diluents, with UV detection at 210 nm.

Example 1c

The same procedure was used as that of Example 1b with a few modifications. The reaction time after addition of Sodium Hydroxide was reduced from 72 hours to 24 hours. The two aliquots of DI water used to wash the retentate were reduced to 150 grams each.

The dried product resulting from this example weighed 84 grams. The purity was approximately the same as that of Example 1b.

Example 2

Conversion of Form 1 to Form 2

Crystalline rebaudioside B Form 1 was obtained as shown in Example 1a. Form 1 (100 mg) was suspended in 5 mL pure ethanol and heated to 60° C. for 2 hours with magnetic stirring. The solution was then cooled down to room temperature (25° C.). The solution was filtered and the retentate was air dried. The resulting crystalline composition was crystalline Form 2 rebaudioside B.

Example 3

Conversion of Form 1 to Form 3

Crystalline rebaudioside B Form 1 was obtained as shown in Example 1a. Form 1 (approximately 50 mg) was suspended in a 5 mL solution of 90% ethanol and 10% water and heated to 60° C. for 2 hours with magnetic stirring. The solution was then filtered, and any remaining solvent was allowed to evaporate from the retentate. The resulting crystalline composition was crystalline Form 3 rebaudioside B.

Example 4

Conversion of Form 1 to Form 4

Crystalline rebaudioside B Form 1 was obtained as shown in Example 1a. Form 1 (20 mg) was suspended in a 5 mL water and stayed at room temperature (25° C.) for 24 hours with stirring. The solution was filtered and the retentate was air dried. The resulting crystalline composition was crystalline Form 4 rebaudioside B.

We claim:

1. A crystalline Form 2 rebaudioside B, having an X-ray powder diffraction pattern substantially similar to the X-ray diffraction pattern shown in FIG. 6.

2. The crystalline Form 2 rebaudioside B of claim 1, wherein the crystalline Form 2 rebaudioside B has a solubility in water at 25° C. of less than 0.5 mg of the rebaudioside B crystal form/mL water.

3. The crystalline Form 2 rebaudioside B of claim 1, wherein the crystalline Form 2 rebaudioside B has a solubility in ethanol at 25° C. ranging from 2 to 4 mg of the rebaudioside B crystal form/mL ethanol.

4. A crystalline Form 3 rebaudioside B, having an X-ray powder diffraction pattern substantially similar to the X-ray diffraction pattern shown in FIG. 10.

5. The crystalline Form 3 rebaudioside B of claim 4, wherein the crystalline Form 3 rebaudioside B has a solubility in water at 25° C. of less than 0.5 mg of the rebaudioside B crystal form/mL water.

6. The crystalline Form 3 rebaudioside B of claim 4, wherein the crystalline Form 3 rebaudioside B has a solubility in ethanol at 25° C. ranging from 8 to 12 mg of the rebaudioside B crystal form/mL ethanol.

7. A crystalline Form 4 rebaudioside B, having an X-ray powder diffraction pattern substantially similar to the X-ray diffraction pattern shown in FIG. 14.

* * * * *